United States Patent [19]

Dorn

[11] Patent Number: 4,927,749

[45] Date of Patent: May 22, 1990

[54] REAGENT FOR CELL SEPARATION

[75] Inventor: Allan R. Dorn, Bethany, Okla.

[73] Assignee: Jeanette Simpson, Tulsa, Okla.

[21] Appl. No.: 849,819

[22] Filed: Apr. 9, 1986

[51] Int. Cl.$^5$ .......................... A01N 1/02; C12N 1/02
[52] U.S. Cl. ........................................ 435/2; 424/529; 424/534; 424/561; 428/405; 435/261
[58] Field of Search ................ 428/405; 435/181, 261, 435/2; 424/101

[56] References Cited

U.S. PATENT DOCUMENTS

| | | |
|---|---|---|
| 3,795,313 | 3/1974 | Kirkland et al. |
| 3,977,982 | 8/1976 | Hertl |
| 3,983,299 | 9/1976 | Regnier |
| 3,984,349 | 10/1976 | Meiller et al. |
| 4,034,072 | 7/1977 | Mjos et al. |
| 4,049,496 | 9/1977 | Henry |
| 4,108,603 | 8/1978 | Regnier et al. |
| 4,172,803 | 10/1979 | Ichikawa et al. |
| 4,177,315 | 12/1979 | Ubersax |
| 4,188,451 | 2/1980 | Humphrey, Jr. |
| 4,190,535 | 2/1980 | Luderer et al. |
| 4,406,792 | 9/1983 | Glad et al. |
| 4,415,631 | 11/1983 | Schutijser ............................ 428/405 |
| 4,454,056 | 6/1984 | Kittelmann ......................... 428/405 |
| 4,457,782 | 7/1984 | Honda et al. |
| 4,474,704 | 10/1984 | Sawicki .............................. 556/400 |
| 4,487,700 | 12/1984 | Kanter |
| 4,644,077 | 2/1987 | Gupta ................................. 556/400 |

FOREIGN PATENT DOCUMENTS

WO820240 3/1982 PCT Int'l Appl.

OTHER PUBLICATIONS

Skopenko, V. V., et al., "Immobilization of 1,10--Phenanthroline and 2,2'-Dipyridyl on a Silica Surface," 22 *Physical Organic Chemistry*, vol. 102, 1985, p. 585, Abstract No. 102:131417p.

Voroshilova, O. I., et al., "Synthesis and Study of Silica Supports with a Surface Modified by Gamma-Aminopropyl Groups," 66 *Surface Chemical, Colloids*, vol. 92, 1980, p. 371, Abstract No. 92:204090p.

Lynn, Merrill, et al., "Chemically Bonded Packings for Chromatography," Abstract No. 59239f, *Chemical Abstracts*, vol. 82, p. 88, 1975.

"Isopycnic Centrifugation of Mammalian Metaphase Chromosomes in Nycodenz" in *Experimental Cell Research*, 152:204-211 (1984) by Gollin and Wray.

"A Cold Silanization Method for Preparation of Medium Polarity Capillary Columns" in *Journal of High Resolution Chromatography and Chromatography Communications*, 6:60-63 (1983) by Traitler.

"Sedimentation of Cells in Colloidal Silica (Percoll)" in *Cell Separation: Methods and Selected Applications*, vol. 1, pp. 115-152, Academic Pres, 1982 by Pertoft and Laurent.

"Efficient Separation of Human T Lymphocytes from Venous Blood Using PVP-Coated Colloidal Silica Particles (Percoll)" in *Journal of Immunological Methods*, 38:43-51 (1980) by Feucht et al.

"Separation of Functional Subpopulations of Murine and Human Lymphoid Cells on Colloidal Silica Density Gradients I. Preparation of the Ludox AM ® Gradient Material and Characterization of Separation Capacities" in *Journal of Immunological Methods*, 28:277-292 (1979) by Lundak et al.

"Density Gradients Prepared from Colloidal Silica Particles Coated by Polyvinylpyrrolidone (Percoll)" in *Analytical Biochemistry*, 88:271-282 (1978) by Pertoft et al.

(List continued on next page.)

Primary Examiner—Sam Rosen
Attorney, Agent, or Firm—Richards, Medlock & Andrews

[57] ABSTRACT

Cell separation compositions and associated methods effective for separating cells from various biological specimens such as blood are disclosed. The biological specimens are contacted with the cell separation compositions and centrifuged. The cells are separated based upon their buoyant density in the cell separation composition.

11 Claims, 2 Drawing Sheets

OTHER PUBLICATIONS

"The Viability of Cells Grown or Centrifuged in a New Density Gradient Medium, Percoll (TM)", in *Experimental Cell Research*, 110:449–457 (1977) by Pertoft et al.

"The Effect of Surface Aluminosilicate Ions on the Properties of Colloidal Silica" in *Journal of Colloid and Interface Science*, 55:25–34 (1976) by Iler.

"Factors Affecting the Separation of Photosynthetically Competent Chloroplasts in Gradients in Silica Sols" in *Archives of Biochemistry and Biophysics*, 168:289–301 (1975) by Morgenthaler.

"Identification, Enumeration and Isolation of Band T Lymphycytes from Human Peripheral Blood" in *Clinical Immunology and Immunopathology*, 3:584–597 (1975) by Aiuti et al.

"Enumeration of Absolute Numbers of T and B Lymphocytes in Human Blood" in *Scandanavian Journal of Immunology*, 3:161–172 (1974) by Brown and Greaves.

"Coacervantes of Polyvinyl Alcohol and Colloidal Silica" in *Journal of Colloid and Interface Science*, 51:388–390 (1974) by Iler.

"The Separation of Rat Liver Cells in Colloidal Silica–Polyethylene Glycol Gradients" in *Experimental Cell Research*, 57:338–350 (1969) by Pertoft.

"Separation of HeLa Cells by Colloidal Silica Density Gradient Centrifugation" in *Journal of Cell Biology*, 55:579–585 (1972) by Wolff and Pertoft.

"Separation of Various Blood Cells in Colloidal Silica–Polyvinylpyrrolidone Gradients" in *Experimental Cell Research*, 50:355–368 (1968) by Pertoft et al.

"Separation of Blood Cells Using Colloidal Silica–Polysaccharide Gradients" in *Experimental Cell Research*, 46:621–623 (1966) by Pertoft.

"Fractonation of Cell Organelles in Silica Cell Gradients" in *Methods in Cell Biology*, vol. XV, pp. 177–201 (1977) by Schmidt et al.

"Isopycnic Separation of Cells and Cell Organelles by Centrifugation and Modified Colloidal Silica Gradients" in *Methods of Cell Separation*, vol. 1, Catsimpoolas, N., Editor, Plenum Press, New York, pp. 24–65 (1977) by Pertoft and Laurent.

"Problems Connected with the Separation of Different Kinds of Cells" in *International Review of Experimental Pathology*, 14:91–204 (1975) by Pretlow et al.

"Physical Procedures for the Separation of Animal Cells" in *Annual Reviews of Biophysics and Bioengineering*, 1:93–130 (1972) by Shortman.

"Percoll® Methodology and Applications", Pharmacia Fine Chemicals ©1982.

"Ludox® Colloidal Silica".

"Isolymph TM", Gallard–Schlesinger Chemical Mfg. Corp.

"Nycodenz®", Nyegaard, Dec. © 1982.

"Ficoll–Paque® for in vitro Isolation of Lymphocytes", Pharmacia Fine Chemicals, © 1983.

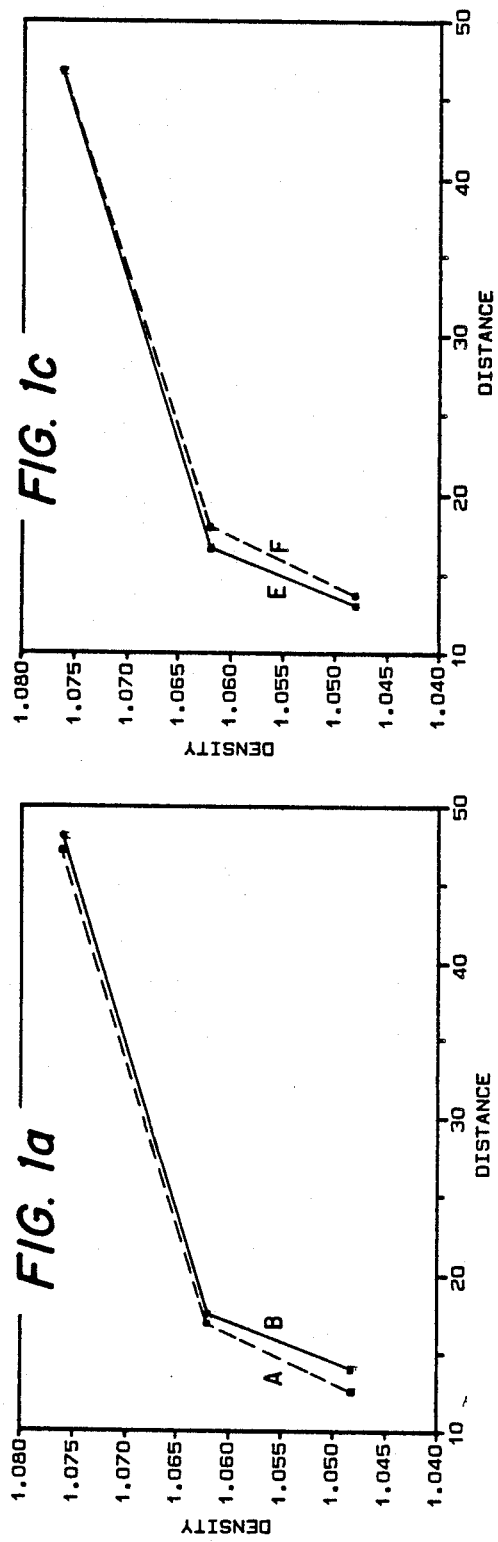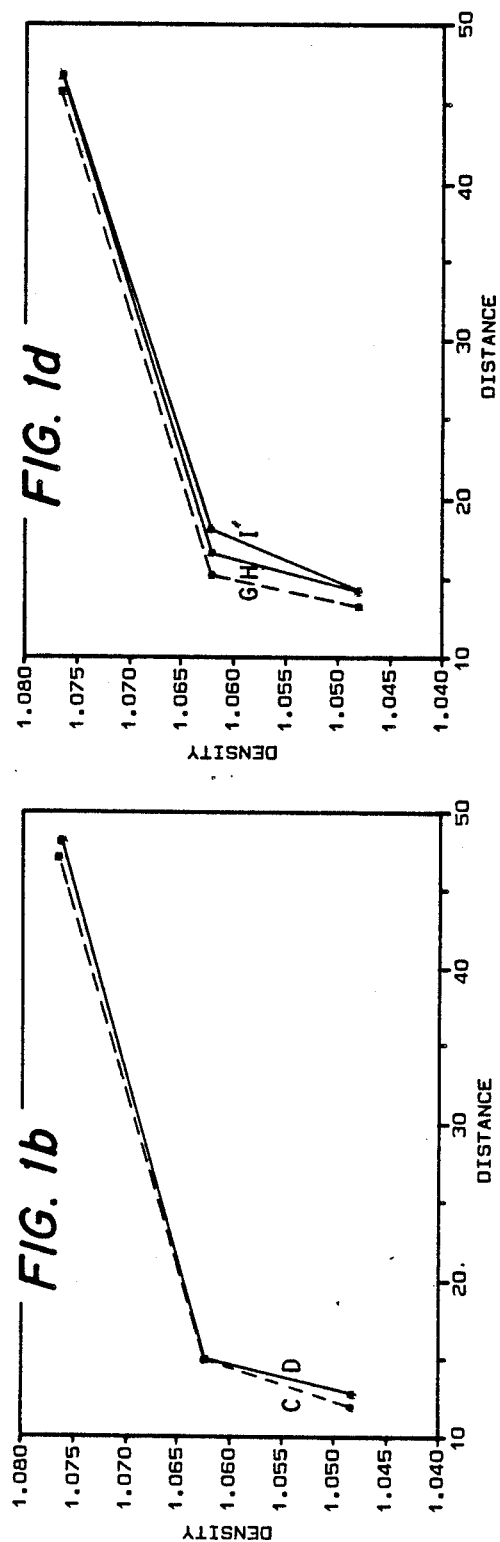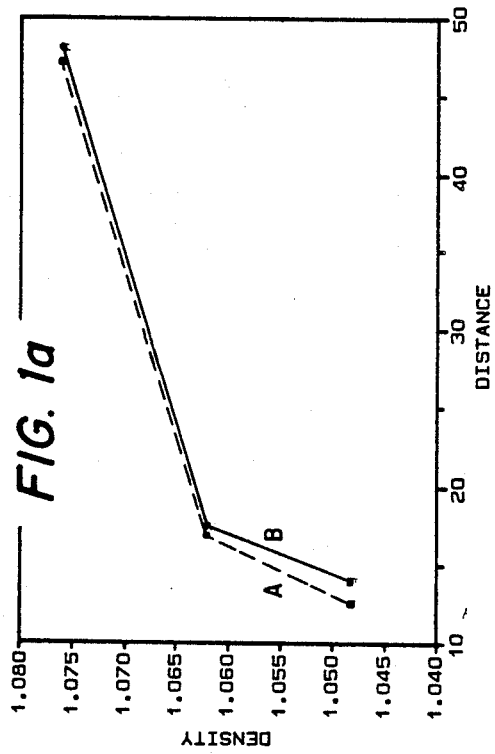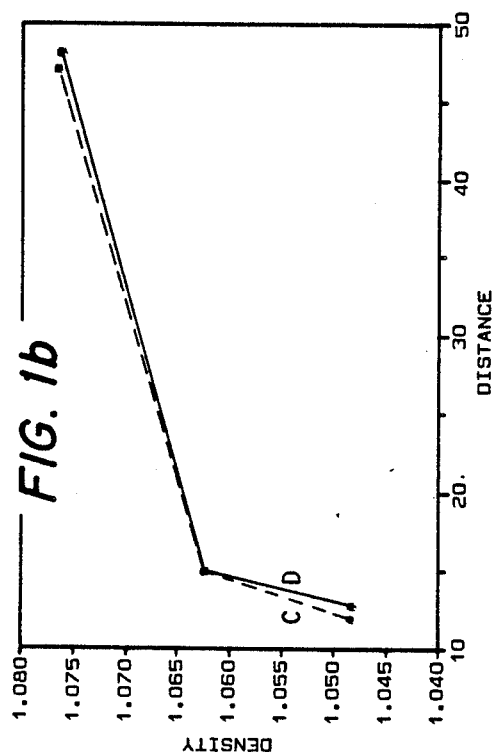

REAGENT FOR CELL SEPARATION

TECHNICAL FIELD

This invention relates to a novel composition for the separation and purification of biological cells and subcellular components. In particular, this invention relates to a novel composition for isolating specific cell types or specific subcellular components based upon their buoyant density. In still another aspect, this invention relates to a novel method and means for use in the isolation of specific cell types and specific subcellular components which provides improved purity of recovered cells and subcellular components.

BACKGROUND OF THE INVENTION

Separating components of biological fluids and tissues is often necessary for clinical diagnostic procedures, scientific research, and occasionally treatment of patients. In the clinical diagnostics field, for example, there is a need for compositions and methods which permit rapid isolation of purified lymphocytes for tissue typing procedures, immunologic function tests, and various other procedures. Basic research also requires purified lymphocytes as well as other cell types from blood. In addition, studies on cultured cells and subcellular components such as plasmids, DNA, chromosomes, mitochondria and other subcellular components also require highly purified preparations.

Separation and purification might be effected in several ways. However, since the isolated cells are often used in procedures which require viable cells, it is important that the functions of the cells so isolated be unimpaired. To insure viability of the cells and unimpaired biological function of cells and subcellular components, it is important to avoid introducing possible interfering substances in the course of the separation procedure. For example, isolated lymphocytes used in histocompatibility tests are stimulated with various mitogens. The medium used must not in itself be a mitogen since this will affect the validity of the measurements of DNA synthesis.

Density gradient centrifugation is one technique used for separation of biological cells and subcellular components. It is highly desirable that the material chosen for formation of the gradient have certain characteristics which will impart compatability with sensitive biological materials. Gradient materials which have been employed in the art include sucrose, dextran, bovine serum albumin (BSA), Ficoll (registered trademark of Pharmacia), iodinated low molecular weight compounds such as Metrizamide and heavy salts such as cesium chloride. Most of these materials, however, have undesirable characteristics which potentially may impair the biochemical functions of the desired isolated fractions. For example, some currently available blood separation media contain erythrocyte aggregation polmers which may decrease mitogen responsiveness of isolated lymphocyte preparations (*J. Immunol. Meth.* 38:43–51, 1980). These materials may also form solutions of undesirably high osmolality or viscosity. Cell aggregation is often caused by BSA at physiological pH (7.4) and it is undesirable to employ reduced pH (5.1) because it introduces other problems such as cell swelling (which alters cell density) and possible impairment of cell function. It is also expensive for use in large scale separations. Ficoll may similarly cause cellular aggregation which can be remedied only by use of a dispersing agent, or undesirably, lowering of the pH. Ficoll is also highly viscous, making it difficult to generate a linear isoosmotic gradient with it. It is also difficult to separate cells with very similar buoyant densities with any of these materials, even with the use of discontinuous gradients.

A density gradient material which has been used with some success for cell separation is colloidal silica. Colloidal silica is an aqueous suspension of colloidal particles formed by polymerization of monosilicic acid from $SiO_2$ dissolved in water. Individual particles average 130–140 Å in size and generally range from about 30 to 220 Å. The colloidal suspension is most stable for storage at pH 8–10 at which the colloidal particles have a net negative charge. It is, however, not entirely satisfactory. Colloidal silica solutions are irreversibly precipitated on freezing and form gels in the presence of proteins under certain ionic conditions such as above 0.1M NaCl at pH 5–7. Unmodified silica gels also exhibit toxicity towards a number of cell types including macrophages and red blood cells. Numerous attempts have been made to reduce this toxicity and to increase the stability of the colloid in salt solutions and protein at physiological pH by coating the colloidal silica with a polymer. Polymers such as dextran (*Exp. Cell Res.*, 50: 355-368 (1968)), polyvinyl alcohol (PVA) (*J. Coll. and Interface Sci.*, 51: 388-393 (1974)), polyethylene glycol (PEG) (*Exp. Cell Res.*, 57: 338-350 (1969), *Arch. Biochem. Biophys.*, 168: 289-301 (1975)), dextran sulfate, methyl cellulose, carboxymethyl cellulose (*Exp. Cell Res.*, 50: 355-368, (1968)), polyvinylpyrrolidone (PVP) (*Exp. Cell Res.*, 46: 621-623 (1966); *Exp. Cell Res.*, 50: 355-368 (1968); *J. Cell Biol.*, 55: 579-585 (1972); *Exp. Cell Res.*, 110: 449-457 (1977)) and a mixture of PEG, BSA and Ficoll (*Arch. Biochem. Biophys.*, 168: 289-301 (1975)) have been used as coatings for silica sols such as Ludox (registered trademark of DuPont).

Merely coating the silica particles with polymer also presents problems. The coating procedure requires the use of an excess of free polymer in the solution. The excess polymer increases the osmolality and viscosity of the solution. It is also difficult to remove the polymer from the purified biological material. Furthermore, while the morphological characteristics of cells and organelles purified with polymer-coated colloidal silica are generally acceptable, the biochemical characteristics are often imparied. For example, lymphocytes isolated with mixtures of colloidal silica and PVP have a decreased incorporation of radioactive thymidine as compared to cells in control medium. *Exp. Cell Res.*, 50: 353 (1968).

Another approach to reducing the toxicity of colloidal silica has been to chemically modify the surface of the silica particles. An example of a chemically modified colloidal silica is Ludox AM (registered trademark of DuPont) in which aluminum is chemically incorporated into the colloidal silica. *J. Colloid and Interface Science*, 55:25 (1975). This preparation is reportedly stable over a wide pH range, however it is not suitable for cell separation unless it is first extensively dialysed and/or treated with charcoal to render it nontoxic to lymphoid cells and useful for separating lymphocyte subpopulations. *J. Immunological Methods*, 28:277 (1979). Ludox AM reportedly makes only a minor contribution to osmolality and it is therefore possible to construct isoosmotic gradients using this compound. Ludox AM has several drawbacks, however. The gradient material must be stored under sterile conditions since it will support the growth of various microorganisms. Antibiotics and antifungal agents must be added to the gradient material to inhibit the growth of contaminating microorganisms which may be found in various lymphoid tissues. Furthermore, in order to adequately separate subpopulations of lymphoid cells it is necessary to use discontinuous gradients. *J. Immunological Methods*, 28:277-292 (1979). Limitations inherent in discontinuous density separation (*Ann. Rev. Biophys. Bioeng.* 1:93-130, 1972; *Int. Rev. Exp. Path* 14:91-204, 1975; "Automated Cell Identification and Cell Sorting", Academic Press, pp. 21-96, 1970) may contribute to lower lymphocyte recoveries, which may result in altered lymphocyte ratios (*Scand. J. Immunol.* 3:61, 1974; *Clin. Immunol. Immunopath.* 3:584-597, 1975). Furthermore, discontinuous gradients are made from individual solutions of varying densities. It is extremely time-consuming to make up the various solutions of the correct density. Generation of density gradients by centrifugation also requires speeds of 20,000 to 30,000 rpm.

Another chemically modified colloidal silica which is commercially available is Percoll (registered trademark of Pharmacia) which is a silica particle to which a layer of PVP is hydrogen bonded *Anal. Biochem.*, 88: 271-282 (1978). Percoll has been used widely for separating blood cell components as well as subcellular organelles from a variety of sources. As supplied by the manufacturer, Percoll has a density of $1.130 \pm 0.005$ g/cm$^3$, a pH of $9.0 \pm 0.5$ and an osmolality of $<25$ mOsM/kg. The Percoll is made isoosmotic by adding physiological saline and adjusting the pH to 7.0-7.4 by adding acid or base. The density must also be carefully adjusted. If cells have a buoyant density greater than 1.11-1.12 g/cm$^3$ then the Percoll must be concentrated. The usual technique for using Percoll is either to preform the gradient by layering or by using a gradient former or by centrifugation (generally requires 20,000 to 30,000 rpm) prior to addition of the sample. Alternatively, the cell preparation may be mixed directly with diluted isoosmotic Percoll prior to centrifugation.

Several factors limit the ease, performance and utility of Percoll as a blood cell separation medium, however. Percoll has a strong absorbency in the ultraviolet region due to the PVP. This is a significant disadvantage when density gradients are analyzed for nucleic acids and proteins by spectrophotometric methods. PVP also gives a high background in the Lowry method for protein determination. *Cell Separation: Methods and Selected Applications*, Vol I. 115, 134 (1982). Percoll is somewhat stable at physiological pH and ionic strength, however it is not stable to autoclaving after it is made isoosmotic (by the addition of salt, acid and base), and in dilute solutions it tends to aggregate. The latter problem is due to dissociation of PVP from the silica surface and can be prevented by the addition of low concentrations of free PVP. As noted above, free PVP has a negative effect on at least some cell functions. It is also difficult to separate cells which have only small differences in buoyant density with Percoll.

It has now been found that a novel colloidal silica preparation useful for the separation of biological materials can be prepared by using a novel chemical modification technique. The composition is made by reacting an organosilane under aqueous conditions with nonporous colloidal silica at an elevated temperature and at alkaline pH to form a covalent linkage between the silica particle and the organosilane. The composition may be used for isolating specific cell types or specific subcellular components based upon their buoyant density. The composition provides for improved purity of recovered cells and subcellular components and for decreased sample processing time. A composition which combines different sizes of reagent-modified silica particles can also be prepared. This combination composition offers the further advantage of separating cells and cellular components with only minute differences in buoyant density. This type of separation has up until now been impossible or impractical to achieve. A further composition which can be prepared consists of reagent-modified silica particles to which purified antibody has been coupled. This antibody-modified composition offers the advantage of separating cells and cell components based upon their antigenic determinants as well as their complement of any other cellular component, such as peptide hormone receptors, to which antibodies can be raised.

The composition has several desirable characteristics. The reagent modification reduces the toxicity of the colloidal silica and eliminates aggregation of the colloidal silica particles in the presence of physiological salt and protein. The composition is compatible with biological material and is suitable for density separation of both cellular and subcellular biological particles. It permits the use of either preformed gradients or in situ density gradient formation and rapid cell separation using relatively low-speed centrifugation. The composition is of physiological ionic strength and pH, isoosmolar, of low viscosity, and in a density range of 1.0 to 1.4 g/cm$^3$. It is stable over a wide range of temperature and pH values. As evidence of its stability, the composition is completely stable to autoclaving at physiological conditions. Furthermore, it is soluble or dispersible in aqueous solutions, is easily removed from biological specimens, and is of low cost.

The methods for use of this composition also offer several advantages. Traditional blood separation procedures require careful blood layering technique. The technical skill required to perform blood separation with this composition is much less than with other techniques. For example, no layering is required with the in situ technique. The material to be separated is simply mixed with the reagent-modified colloidal silica and centrifuged. To separate mononuclear cells from whole blood, the inherent density difference which exists between mononuclear cells and other cellular elements present in peripheral blood is used. A continuous density gradient suitable for mononuclear cell separation is formed upon centrifugation by the sedimentation of the reagent-modified colloidal silica particles. Rapid gradient formation is due to the high sedimentation rate of the particles used ($\geq 200$ Å diameter) for this type of separation. Cell separation is accomplished by the movement of the peripheral blood cells during centrifugation to their respective buoyant densities within the continuous density gradient. The separation technique is inexpensive and requires little if any specialized equipment other than a clinical centrifuge.

SUMMARY OF THE INVENTION

According to the invention, I have discovered a method for making and using nonporous colloidal silica particles coated with a reagent which imparts a nontoxic, non-ionic hydrophilic surface to the silica particles. The resulting reagent-modified colloidal silica can be used for separating cells and subcellular components from all types of body fluids such as blood, bone marrow, spinal and pleural fluids, and semen, as well as dispersed tissue specimens, cultured cells and any other source of biological cells and their components.

According to one embodiment of the subject invention, a novel technique for the manufacture of a reagent-modified colloidal silica is provided which includes the steps of admixing colloidal silica with an organosilane reagent at elevated temperatures and alkaline pH in aqueous media such that the organosilane is coupled to the colloidal silica. The resulting reagent-modified colloidal silica is freed of reaction by-products by activated charcoal adsorption and then deionized. The reagent-modified colloidal silica is then reheated in order to form additional covalent attachments between the reagent and the reagent-modified colloidal silica. The osmotic pressure and pH are adjusted to be compatible with biological materials. The reagent-modified colloidal silica is then diluted with a buffer to a density appropriate for the biological material to be separated. The organosilane, covalently linked to the surface of the silica, reduces the toxicity of the colloidal silica, and prevents coagulation of the colloidal silica particles in the presence of protein at physiological pH and salt concentration.

According to another embodiment of the subject invention, a novel technique for the manufacture of antibody-coupled reagent-modified colloidal silica using a thiol reagent is provided which includes the steps of admixing reagent-modified colloidal silica with a thiol reagent in aqueous media such that thiol groups are incorporated onto the surface of the reagent-modified colloidal silica. The thiol groups are further reacted with a succinimide to provide a linkage to which Protein A is then coupled. An antibody is then coupled to the Protein A to form antibody-modified colloidal silica. The use of antibody-modified colloidal silica permits the separation, from a cell mixture such as blood, of component cells with antigenic determinants to which the antibody can bind.

According to another embodiment of the subject invention, a novel technique for the manufacture of antibody-modified colloidal silica using carbodiimide is provided which includes the steps of reacting reagent-modified colloidal silica with a carbodiimide in aqueous media to form a linkage arm to which Protein A is subsequently coupled via an amide bond. An antibody is then coupled to the Protein A to form antibody-modified colloidal silica.

According to another embodiment of the subject invention, a novel technique for the separation of component cells from mixtures of biological cells such as whole blood or other biological fluids is provided which includes the steps of contacting a diluted cell mixture with a diluted reagent-modified colloidal silica composition having a final density which spans the buoyant density of the component cells of the cell mixture to be separated by layering the cell mixture on top of the composition, centrifuging the cell mixture and composition in a swinging bucket rotor to effect cell separation, and collecting the component cells which migrate to a characteristic buoyant density for a specific cell type where they form a band at that density. For example, lymphocytes can be separated from other cell types in a blood sample. Typically, lymphocytes have a buoyant density of 1.060–1.074 g/cm$^3$, and will form a cell band at the density interface. Other cell types will penetrate into the gradient material. The cell band can be removed, and the cells washed, pelleted and resuspended in a medium suitable for growth or metabolic studies, or other experimentation.

According to another embodiment of the subject invention, a novel technique for the separation of component cells from mixtures of biological cells such as whole blood or other biological fluids is provided and includes admixing a sample of a cell mixture with the diluted reagent-modified colloidal silica composition and centrifuging in a fixed angle rotor or swinging bucket rotor. A continuous density gradient is formed upon centrifugation. The component cells migrate to characteristic buoyant densities within the gradient and form bands of cells at densities characteristic of the specific cell types. For example, mononuclear cells may be separated from other cells in a blood sample using this in situ separation technique. The mononuclear cells form a cell band just below the meniscus. The mononuclear band as well as other bands of cells can each be collected, washed, pelleted, and resuspended in a medium suitable for growth or metabolic studies, or other experimentation.

According to another embodiment of the subject invention, a novel technique for the separation of biological cells or subcellular components with only small differences in buoyant density is provided. The technique includes the steps of admixing reagent-modified colloidal silica particles of differing sizes with a mixture of cells such as a blood sample, buffy coat or bone marrow, admixing the cell mixture and the reagent-modified colloidal silica composition, centrifuging the admixture to generate a density gradient and thereafter collecting the individual bands of cells which form at specific characteristic buoyant densities. The cells so collected are then washed, pelleted, and resuspended in a medium suitable for growth or metabolic studies, or other experimentation. For example, B and T lymphocytes may be separated from other cells in a blood sample. B cells have a lower density range than T cells. The T and B cells can be separated by choosing a gradient shape such that the B cells band at a sharp break in the gradient, and the T cells band separately at a higher density. Inclusion of small reagent-modified colloidal silica particles (those made from colloidal silica particles of ≦about 80 Å) in the gradient expands or narrows the lower density range while inclusion of larger reagent-modified colloidal silica particles (those made from colloidal silica particles of ≧about 200 Å) compresses the higher density range of the gradient. Thus, by choosing the proper initial density and expanding select regions of the density gradient with reagent-modified colloidal silica particles made from the appropriate particle size, B and T cells can be separated. This approach can also be used to separate NK cells from B and T cells. Separation of B, T, and NK cells can be followed by staining the cells with fluorescent monoclonal antibodies for B, T, and NK cells.

According to another embodiment of the subject invention, a novel technique for the separation of biological cells or cellular components with differing antigenic determinants is provided. Colloidal silica with a large particle size (about 600 Å) is used for preparing the antibody-modified colloidal silica particles. The antibody-modified colloidal silica is admixed with a cell mixture. The admixture is incubated for a sufficient time to permit the antibody-modified colloidal silica to bind to the antigenic sites on the component cells. The admixture is then centrifuged through a cell separation composition. The antibody-modified colloidal silica with attached cells can be recovered from the bottom of the gradient. Attached cells can be removed from the antibody-modified colloidal silica prepared using a thiol reagent by treatment with a sulfhydryl reducing agent. If the antibody-modified colloidal silica was prepared by coupling the Protein A directly onto the surface of the reagent-modified colloidal silica via an amide bond, the attached cells may be removed by treatment with ethanolamine. Following removal from the antibody-modified colloidal silica, the cells can be washed and resuspended in a medium suitable for growth or metabolic studies, or other experimentation.

BRIEF DESCRIPTION OF THE DRAWINGS

FIGS. 1a, b, c, d and are graphic depictions of the shape of the gradients obtained when distinct populations of diluted reagent-modified colloidal silica are admixed.

DETAILED DESCRIPTION OF THE PREFERRED EMBODIMENTS

Figure 2:
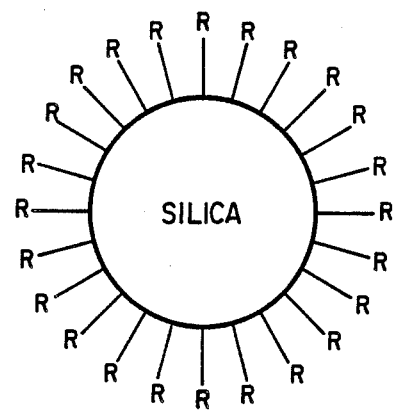
FIG. 2 is a schematic representation of reagent-modified colloidal silica wherein the attached organosilane reagent groups are represented by "R".

Reagent-modified colloidal silica compositions are disclosed which are suitable for separation of biological cells and cellular components. The use of "distinct populations", as defined below, of the compositions will decrease the time required to obtain isolated cells and cellular components as well as increase the purity of the resulting isolates. The use of mixtures of distinct populations of the reagent-modified colloidal silica compositions will permit the separation of cell types with very similar buoyant densities. The use of distinct populations of reagent-modified colloidal silica which have been further modified by coupling to purified monoclonal antibodies will permit the separation of cells based upon their complement of antigenic determinants.

The size of the non-porous colloidal silica particles used in the coupling reaction varies from about 30 Å to about 600 Å. The starting material for each individual composition comprises a plurality of colloidal silica particles which are all about the same diameter. However, this "population" of colloidal silica particles has a size range that can be represented by a distribution curve such as can be derived by using particle sizing methods known in the art. Most particles in the population will be of the size at the peak of the distribution curve, but the entire curve represents the population. The sizes specified for the populations are the sizes indicated in the manufacturer's specifications. The actual sizes of the populations as received from the manufacturer may vary from lot to lot. To accommodate the size variations, each population is referred to as "about x Å" where x is the particle size designation indicated in the manufacturer's catalogues and product specifications. Colloidal silica particles usable in accordance with the present invention include the material sold under the designation "Nyacol" by Nyacol Products, Inc. (Worchester, Mass.), which material is an aqueous suspension of colloidal particles formed by polymerization of monosilicic acid from $SiO_2$ dissolved in water. Once covalently linked to the modifying reagent, the particles become a collection of reagent-modified colloidal silica particles each having a buoyant density within a defined range. The resulting buoyant density range and most preferable buoyant density of particle populations following coupling with the modifying reagent are as shown in Table 1.

TABLE 1

| | Bouyant Density of Reagent-Modified Colloidal Silica Populations | |
|---|---|---|
| | Reagent-Modified Colloidal Silica | |
| Unmodified Silica Particle size (Å) | Preferable Buoyant Density Range (g/m³) | Most Preferable Buoyant Density (g/cm³) |
| 30 | 1.06–1.16 | 1.11 |
| 40 | 1.046–1.146 | 1.096 |
| 70 | 1.0674–1.1674 | 1.1174 |
| 80 | 1.115–1.215 | 1.165 |
| 120 | 1.119–1.219 | 1.169 |
| 130 | 1.112–1.212 | 1.162 |
| 140 | 1.172–1.272 | 1.222 |
| 150 | 1.219–1.319 | 1.269 |
| 200 | 1.139–1.239 | 1.189 |
| 220 | 1.12–1.22 | 1.17 |
| 600 | 1.33–1.43 | 1.38 |

A population of reagent-modified colloidal silica particles that can be distinguished from another population by the diameter of the particles used in the coupling reaction and its buoyant density following coupling with the modifying reagent is referred to as a "distinct population" even though the characteristics of some of the particles in two distinct populations may be similar. One or more distinct populations may be admixed to form a cell separation composition admixture with particular separation properties.

The reagent which is covalently linked to the colloidal silica particles may be any organosilane reagent. Organosilanes are the only compounds which can form stable covalent siloxane bonds (Si-O-Si) with the silanol groups on the surface of the colloidal silica. The functional group in the organosilane must be non-ionic and hydrophilic. Ionic functional groups would be undesirable since the ionic charge would be sensitive to changes in pH and salt, thus resulting in gelling. Hydrophobic functional groups actually sensitize the colloidal silica to gelling at neutral pH and physiologic salt concentration. Hydrophilic functional groups bind $H_2O$ to the colloid surface. The bound $H_2O$ serves as a protective shell which is independent of changes in pH, ionic strength and protein, and thus protects the colloid against gellation.

The organosilane imparts a "non-toxic," non-ionic hydrophilic surface to the silica particles. Non-toxic means that the composition does not affect the integrity or the function of the biological material to be separated. Examples of organosilanes which can be used are listed in Table 2. The preferred organosilane is gamma-glycidoxypropyltrimethoxysilane.

As can be seen from the examples given in the following table, examples of suitable organosilane reagents have the general formulas $(X)_3-Si-(CH_2)_3-Y$ or $(X)_3-Si-(CH_2)_2-Y$. X may be selected from $(H_3CO)$, $(Cl)$, $(H_5C_2O)$, $(H_3CCO_2)$, or $(H_3C)$. The Si atom has a valence of 4 as indicated in the formula; therefore, three X groups will satisfy the valence of Si in the reagent formula. Thus, *X, as used in the following table, indicates that the valence of Si is to be satisfied by selecting sufficient additional X groups from the group consisting of $H_3CO$, $Cl$, $H_5C_2O$, $H_3CCO_2$ or $H_3C$. "Y" is given as part of the main formula in each section. Thus, examples of suitable Y groups are selected from the group consisting of

OCH$_2$CHCH$_2$O, O$_2$CCH$_3$, N(CH$_2$CH$_2$OH)$_2$, CO$_2$CH$_3$,

NH(CH$_2$)$_2$NH(CH$_2$)$_2$CO$_2$CH$_3$, NHCOCH$_2$NHC(CH$_3$)O,

N—CH$_2$—CH$_2$—O—CH$_2$—CH$_2$, and N—CH=CH—CH=CH.

TABLE 2

| Organosilanes Which Can be Used to Prepare Reagent-Modified Colloidal Silica | |
|---|---|
| Parent Organosilane | Where X = |
| (a) (X)$_3$—Si(CH$_2$)$_3$—O—CH$_2$CHCH$_2$O | H$_3$CO |
| (γ-glycidoxypropyl)trimethoxysilane | |
| (3-glycidoxypropyl)trichlorosilane | Cl |
| (3-glycidoxypropyl)triethoxysilane | H$_5$C$_2$O |
| (3-glycidoxypropyl)triacetoxysilane | H$_3$CCO$_2$ |
| (3-glycidoxypropyl)methyldi-*X silane | H$_3$C |
| (3-glycidoxypropyl)dimethyl*X silane | (H$_3$C)$_2$ |
| (b) (X)$_3$—Si(CH$_2$)$_2$—O—CH$_2$CHCH$_2$O | |
| (2-glycidoxyethyl)trimethoxysilane | H$_3$CO |
| (2-glycidoxyethyl)trichlorosilane | Cl |
| (2-glycidoxyethyl)triethoxysilane | H$_5$C$_2$O |
| (2-glycidoxyethyl)triacetoxysilane | H$_3$CCO$_2$ |
| (2-glycidoxyethyl)methyldi-*X silane | H$_3$C |
| (2-glycidoxyethyl)dimethyl*X silane | (H$_3$C)$_2$ |
| (c) (X)$_3$—Si(CH$_2$)$_3$—O$_2$CCH$_3$ | |
| 3-acetoxypropyltrimethoxysilane | H$_3$CO |
| 3-acetoxypropyltrichlorosilane | Cl |
| 3-acetoxypropyltriethoxysilane | H$_5$C$_2$O |
| 3-acetoxypropyltriacetoxysilane | H$_3$CCO$_2$ |
| 3-acetoxypropylmethyldi-*X silane | H$_3$C |
| 3-acetoxypropyldimethyl*X silane | (H$_3$C)$_2$ |
| (d) (X)$_3$—Si(CH$_2$)$_2$—O$_2$CCH$_3$ | |
| 2-acetoxyethyltrimethoxysilane | H$_3$CO |
| 2-acetoxyethyltrichlorosilane | Cl |
| 2-acetoxyethyltriethoxysilane | H$_5$C$_2$O |
| 2-acetoxyethyltriacetoxysilane | H$_3$CCO$_2$ |
| 2-acetoxyethylmethyldi-*X silane | H$_3$C |
| 2-acetoxyethyldimethyl*X silane | (H$_3$C)$_2$ |
| (e) (X)$_3$—Si(CH$_2$)$_3$—N(CH$_2$CH$_2$OH)$_2$ | |
| Bis(2-hydroxyethyl)-3aminopropyl-trimethoxysilane | H$_3$CO |
| Bis(2-hydroxyethyl)-3aminopropyl-trichlorosilane | Cl |
| Bis(2-hydroxyethyl)-3aminopropyl triethoxysilane | H$_5$C$_2$O |
| Bis(2-hydroxyethyl)-3aminopropyl-triacetoxysilane | H$_3$CCO$_2$ |
| Bis(2-hydroxyethyl)-3aminopropyl-methyldi-*X silane | H$_3$C |
| Bis(2-hydroxyethyl)-3aminopropyl-dimethyl*X silane | (H$_3$C)$_2$ |
| (f) (X)$_3$—Si(CH$_2$)$_2$—N(CH$_2$CH$_2$OH)$_2$ | |
| Bis(2-hydroxyethyl)-2aminoethyl-trimethoxysilane | H$_3$CO |
| Bis(2-hydroxyethyl)-2aminoethyl-trichlorosilane | Cl |
| Bis(2-hydroxyethyl)-2aminoethyl-triethoxysilane | H$_5$C$_2$O |
| Bis(2-hydroxyethyl)-2aminoethyl-triacetoxysilane | H$_3$CCO$_2$ |
| Bis(2-hydroxyethyl)-2aminoethyl-methyldi-*X silane | H$_3$C |
| Bis(2-hydroxyethyl)-2aminoethyl-dimethyl*X silane | (H$_3$C)$_2$ |
| (g) (X)$_3$—Si(CH$_2$)$_3$—CO$_2$CH$_3$ | |
| 3-(carbomethoxy)propyltrimethoxysilane | H$_3$CO |
| 3-(carbomethoxy)propyltrichlorosilane | Cl |
| 3-(carbomethoxy)propyltriethoxylsilane | H$_5$C$_2$O |
| 3-(carbomethoxy)propyltriacetoxysilane | H$_3$CCO$_2$ |

TABLE 2-continued

| Organosilanes Which Can be Used to Prepare Reagent-Modified Colloidal Silica | |
|---|---|
| Parent Organosilane | Where X = |
| 3-(carbomethoxy)propyl methyl-di-*X silane | H$_3$C |
| 3-(carbomethoxy)propyldimethyl-*X silane | (H$_3$C)$_2$ |
| (h) (X)$_3$—Si(CH$_2$)$_2$—CO$_2$CH$_3$ | |
| 2-(carbomethoxy)ethyltrimethoxysilane | H$_3$CO |
| 2-(carbomethoxy)ethyltrichlorosilane | Cl |
| 2-(carbomethoxy)ethyltriethoxysilane | H$_5$C$_2$O |
| 2-(carbomethoxy)ethyltriacetoxysilane | H$_3$CCO$_2$ |
| 2-(carbomethoxy)ethyl methyl-di-*X silane | H$_3$C |
| 2-(carbomethoxy)ethyl dimethyl-*X silane | (H$_3$C)$_2$ |
| (i) (X)$_3$—Si(CH$_2$)$_3$—NH(CH$_2$)$_2$NH(CH$_2$)$_2$CO$_2$CH$_3$ | |
| Methyl(2-(3-trimethoxysilylpropyl-amino)ethylamino)-3-proprionate | H$_3$CO |
| Methyl(2-(3-trichlorosilyipropyl-aminoethylamino)-3-proprionate | Cl |
| Methyl(2-(3-triethoxysilylpropyl-amino)ethylamino)-3-proprionate | H$_5$C$_2$O |
| Methyl(2-(3-triacetoxysilylpropyl-aminoethylamino)-3-proprionate | H$_3$CCO$_2$ |
| Methyl(2-(3-di-*X methylsilylpropyl-aminoethylamino)-3-proprionate | H$_3$C |
| Methyl(2-(3-*X dimethylsilylpropyl-aminoethylamino)-3-proprionate | (H$_3$C)$_2$ |
| (j) (X)$_3$—Si(CH$_2$)$_2$—NH(CH$_2$)$_2$NH(CH$_2$)$_2$CO$_2$CH$_3$ | |
| Methyl(2-(2-trimethoxysilylethyl-amino)ethylamino)-3-proprionate | H$_3$CO |
| Methyl(2-(2-trichlorosilylethyl-aminoethylamino)-3-proprionate | Cl |
| Methyl(2-(2-triethoxysilylethyl-amino)ethylamino)-3-proprionate | H$_5$C$_2$O |
| Methyl(2-(2-triacetoxysilylethyl-aminoethylamino)-3-proprionate | H$_3$CCO$_2$ |
| Methyl(2-(2-di-*X methylsilylethyl-aminoethylamino)-3-proprionate | H$_3$C |
| Methyl(2-(2-*X dimethylsilylethyl-aminoethylamino)-3-proprionate | (H$_3$C)$_2$ |
| (k) (X)$_3$—Si(CH$_2$)$_3$—NHCOCH$_2$NHC(CH$_3$)O | |
| N-(trimethoxysilylpropyl)acetylglycinamide | H$_3$CO |
| N-(trichlorosilylpropyl)acetylglycinamide | Cl |
| N-(triethoxysilylpropyl)acetylglycinamide | H$_5$C$_2$O |
| N-(triacetoxysilylpropyl)acetylglycinamide | H$_3$CCO$_2$ |
| N-(di-*X methylsilylpropyl)acetyl-glycinamide | H$_3$C |
| N-(*X dimethylsilylpropyl)acetyl-glycinamide | (H$_3$C)$_2$ |
| (l) (X)$_3$—Si(CH$_2$)$_2$—NHCOCH$_2$NHC(CH$_3$)O | |
| N-(trimethoxysilylethyl)acetylglycinamide | H$_3$CO |
| N-(trichlorosilylethyl)acetylglycinamide | Cl |
| N-(triethoxysilylethyl)acetylglycinamide | H$_5$C$_2$O |
| N-(triacetoxysilylethyl)acetylglycinamide | H$_3$CCO$_2$ |
| N-(di-*X methylsilylacetyl)acetyl-glycinamide | H$_3$C |
| N-(*X dimethylsilylethyl)acetyl-glycinamide | (H$_3$C)$_2$ |
| (m) (X)$_3$—Si(CH$_2$)$_3$—N—CH$_2$—CH$_2$—O—CH$_2$—CH$_2$ | |
| N-(3-trimethoxysilylpropyl)morpholine | H$_3$CO |
| N-(3-trichlorosilylpropyl)morpholine | Cl |
| N-(3-triethoxysilylpropyl)morpholine | H$_5$C$_2$O |
| N-(3-triacetoxysilylpropyl)morpholine | H$_3$CCO$_2$ |
| N-(3-di-*X methylsilylpropyl)morpholine | H$_3$C |
| N-(3-*X dimethylsilylpropyl)morpholine | (H$_3$C)$_2$ |
| (n) (X)$_3$—Si(CH$_2$)$_2$—N—CH$_2$—CH$_2$—O—CH$_2$—CH$_2$ | |
| N-(2-trimethoxysilylethyl)morpholine | H$_3$CO |
| N-(2-trichlorosilylethyl)morpholine | Cl |
| N-(2-triethoxysilylethyl)morpholine | H$_5$C$_2$O |
| N-(2-triacetoxysilylethyl)morpholine | H$_3$CCO$_2$ |
| N-(2-di-*X methylsilylethyl)morpholine | H$_3$C |
| N-(2-*X dimethylsilylethyl)morpholine | (H$_3$C)$_2$ |

TABLE 2-continued
Organosilanes Which Can be Used to Prepare Reagent-Modified Colloidal Silica

| Parent Organosilane | Where X = |
|---|---|
| (o) $(X)_3-Si(CH_2)_3-\overset{\lceil\qquad\qquad\qquad\rceil}{N-CH=CH-CH=CH}$ | |
| N-(3-trimethoxysilylpropyl)pyrrole | $H_3CO$ |
| N-(3-trichlorosilylpropyl)pyrrole | Cl |
| N-(3-triethoxysilylpropyl)pyrrole | $H_5C_2O$ |
| N-(3-triacetoxysilylpropyl)pyrrole | $H_3CCO_2$ |
| N-(3-di-*X methylsilylpropyl)pyrrole | $H_3C$ |
| N-(3-*X dimethylsilylpropyl)pyrrole | $(H_3C)_2$ |
| (p) $(X)_3-Si(CH_2)_2-\overset{\lceil\qquad\qquad\qquad\rceil}{N-CH=CH-CH=CH}$ | |
| N-(2-trimethoxysilylethyl)pyrrole | $H_3CO$ |
| N-(2-trichlorosilylethyl)pyrrole | Cl |
| N-(2-triethoxysilylethyl)pyrrole | $H_5C_2O$ |
| N-(2-triacetoxysilylethyl)pyrrole | $H_3CCO_2$ |
| N-(2-di-*X methylsilylethyl)pyrrole | $H_3C$ |
| N-(2-*X dimethylsilylethyl)pyrrole | $(H_3C)_2$ |

The reagent-modified colloidal silica can be further modified by coupling with an antibody, preferably a monoclonal antibody and most preferably a purified monoclonal antibody. First, Protein A is coupled to the surface of the reagent-modified colloidal silica via an amide bond. The antibody then binds to the Protein A to form antibody-modified colloidal silica. Any size colloidal silica may be used; however, the preferred size is the about 600 Å colloidal silica. If the Protein A is coupled to the reagent-modified colloidal silica via an amide bond, then only the reagent-modified colloidal silica prepared using the organosilanes listed in Table 3 may be used.

TABLE 3
Organosilanes Suitable For Preparation of Antibody-Modified Colloidal Silica Coupled Through an Amide Bond

| Parent Organosilane | | Where X is: |
|---|---|---|
| (a) | $(X)_3 Si(CH_2)_3 N(CH_2CH_2OH)_2$ | |
| | Bis (2-hydroxyethyl)-3 amino propyl-trimethoxysilane | $H_3CO$ |
| | Bis (2-hydroxyethyl)-3 amino propyl-trichlorosilane | Cl |
| | Bis (2-hydroxyethyl)-3 amino propyl-triethoxysilane | $H_5C_2O$ |
| | Bis (2-hydroxyethyl)-3 amino propyl-triacetoxysilane | $H_3CCO_2$ |
| | Bis (2-hydroxyethyl)-3 amino propyl-methyldi *X silane | $H_3C$ |
| | Bis (2-hydroxyethyl)-3 amino propyl-dimethyl *X silane | $(H_3C)_2$ |
| (b) | $(X)_3 Si(CH_2)_2 N(CH_2CH_2OH)_2$ | |
| | Bis (2-hydroxyethyl)-2 amino ethyl-trimethoxysilane | $H_3CO$ |
| | Bis (2-hydroxyethyl)-2 amino ethyl-trichlorosilane | Cl |
| | Bis (2-hydroxyethyl)-2 amino ethyl-triethoxysilane | $H_5C_2O$ |
| | Bis (2-hydroxyethyl)-2 amino ethyl-triacetoxysilane | $H_3CCO_2$ |
| | Bis (2-hydroxyethyl)-2 amino ethyl-methyldi *X silane | $H_3C$ |
| | Bis (2-hydroxyethyl)-2 amino ethyl-dimethyl *X silane | $(H_3C)_2$ |

The composition of this invention generally can be made as follows: the colloidal silica is admixed with an organosilane reagent which will stabilize the colloid state. Preferably the colloidal silica is heated to about 75° C. prior to and during the addition of reagent. The aqueous colloidal silica solution can be of any convenient concentration such that when the desired amount of reagent is admixed with the colloidal silica, the silica always remains in excess relative to the reagent. This can be accomplished by timed reagent additions to the colloidal silica. The rate of reagent addition is preferably from about 0.5 to about 2.0 mls reagent per liter of colloidal silica per minute and most preferably is about 0.7 mls reagent per liter colloidal silica per minute.

The quantity of reagent to be used is dependent upon the total number of surface silanols present in the particular colloidal silica to be chemically modified. The total number of surface silanol groups within a particular colloidal silica can be calcuated as follows:

Total surface silanols = volume (mls) × Density (g/ml) × % silica solids (manufac. data) × Surface area, $nm^2$/g (manufac. data) × 4.5 silanols/$nm^2$ (value from the *The Chemistry of Silica: Solubility, Polymerization, Colloid and Surface Properties, and Biochemistry*, pp. 633-636, 1979). One reagent molecule can react and form covalent bonds with one, two or three surface silanol molecules. An estimate of the volume of reagent to use to chemically modify a colloidal silica can be calculated as follows:

Reagent Volume = (Total surface silanols/Avogadro's number)/Z) × (reagent molec. wt.) ÷ ×(reagent density) where Z is preferably 1, 2, or 3 and most preferably Z = 3. The colloidal silica is "fully modified" when Z = 3. To form "partially modified" colloidal silica for use in making antibody-modified colloidal silica prepared with a thiol reagent, about 50-75% of the quantity of reagent calculated to form fully modified colloidal silica is used.

After reagent addition is complete, the reaction mixture is heated at from about 70° C. to about 80° C. with agitation for 1 hours to 3 hours. Reaction by-products are preferably removed by passing the reaction mixture through activated carbon and by deionization of the reaction mixture. Deionization of the reagent-modified colloidal silica is preferably accomplished by passing the reaction mixture through a cation exchange resin (hydrogen form) and through an anion exchange resin (hydroxide form). Any reagent-modified colloidal silica remaining in either the carbon or the resin columns is preferably recovered by passing water through the respective columns. Additional covalent attachments between the reagent and the silica surface can be facilitated by further heating the reagent-modified colloidal silica with vigorous agitation. This step is preferably carried out at from about 90° C. to about 100° C. for 3 hours to 6 hours. It is even more preferably carried out at about 95° C. for 3 hours.

The reagent-modified colloidal silica preparation is then adjusted to physiological osmotic pressure and pH. The osmotic pressure is preferably adjusted using solid sodium chloride and/or potassium chloride. The pH is preferably adjusted with HEPES buffer in the hydrogen and sodium forms. The density of the resulting solution is then adjusted before use with buffer (20 mM, pH 7.4) to form diluted reagent-modified colloidal silica with a final density which spans the density range of the material to be separated.

The buffer in which the reagent-modified colloidal silica is diluted can be any buffer which is "compatible" with the biological material to be separated and purified. In order to be "compatible" the carrier liquid must be of physiological ionic strength and pH, and not affect the structure or function of the material to be separated. Examples of buffers which can be used include N-2 Hydroxyethylpiperazine-N'-2-Ethanesulfonic acid (HEPES), N-N-bis-2-hydroxyethyl-2-aminoethane sulfonic acid (BES), bis-2-hydroxyethylimino-TRIS-hydroxymethylmethane-2-bis-2-hydroxyethylamino-2-hydroxymethyl-1,3-propanediol (BIS-TRIS), 1,3-bis-[TRIS(hydroxymethyl)methylamino]propane (BIS-TRIS-PROPANE), N-2-hydroxyethylpiperazine-N-3-propane sulfonic acid (EPPS), N-2-hydroxyethylpiperazine-N-2-hydroxypropane sulfonic acid (HEPPSO), 3-N-morpholinopropane sulfonic acid (MOPS), piperazine-N-N-bis-2-ethane sulfonic acid (PIPES), piperazine-N-N-bis-2-hydroxypropane sulfonic acid (POPSO), 3-N-TRIS-(hydroxymethyl)methylamino-2-hydroxypropane sulfonic acid (TES).

The reagent-modified colloidal silica or the diluted reagent-modified colloidal can be sterilized by using sterilization methods known in the art. The compositions are stable to autoclaving; however, a preferred method of sterilization is passage through a 0.2 micron filter. The sterilized product can be used under aseptic conditions for cell separation, for example, to separate cells for subsequent growth in culture or for use in tests which require sterility of the starting materials.

The effectiveness of the in situ separation of component cells from a cell mixture by continuous density gradient centrifugation is dependent upon the density of the resulting admixture of the cells and the diluted reagent-modified colloidal silica. For example, when separating mononuclear cells from whole blood, the density of the admixture can be calculated using the following formula:

$$1.067 \text{ g/cm}^3 = \frac{(1.024 \text{ g/cm}^3)(X \text{ ml}) + (Y1 \text{ g/cm}^3)(Y \text{ ml})}{(X \text{ ml} + Y \text{ ml})}$$

wherein 1.067 g/cm$^3$ is the resulting density of an optimal mixture of whole blood and diluted reagent-modified colloidal silica and wherein 1.024 g/cm$^3$ is the effective density of whole blood (the density of blood minus the density contribution by the red blood cells in the blood) and wherein X=volume of blood to be separated and wherein Y1=density of diluted reagent-modified colloidal silica and wherein Y=volume of diluted reagent-modified colloidal silica.

Any combination of whole blood and diluted reagent-modified colloidal silica can be used. The only limitation is that the resulting density of the admixture be about 1.067±0.001 g/cm$^3$. Erythrocyte density is pH dependent. The density of erythrocytes is greatest at pH 7.40±0.03 in diluted reagent-modified colloidal silica. Consequently, the most efficient separation of erythrocytes from mononuclear cells is achieved at this pH.

The structure of the reagent-modified colloidal silica is as follows:

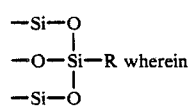

wherein

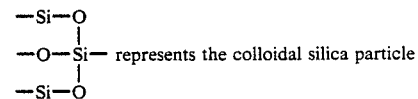

and R is the reagent linked to the colloidal silica particle. When the reagent is gamma-glycidoxypropyltrimethoxysilane, the structure of the reaction product is as follows:

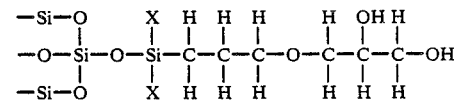

where the two X groups constitute either two —OH groups or preferably one —OH and one additional linkage or more preferably two additional linkages with the silica surface. No cross-linking or polymerization between R groups occurs. The schematic representation of the final colloidal silica particle is shown in FIG. 2 wherein the attached reagent groups are represented by "R".

In use, diluted reagent-modified colloidal silica is contacted in an appropriate manner with a sample containing cells or cellular components to be separated. The choice of which particle size composition to use is based upon the range of the buoyant densities of the cells or cellular components to be separated and the centrifugal force and duration to be used in the separation. The use of larger particle sizes is preferred because it reduces the time and g-force required to generate a density gradient compared with smaller particle sizes. Large particle sizes have a sedimentation rate greater than smaller particle sizes since the sedimentation rate is proportional to the square of the particle diameter. Lower centrifugation times and g-forces reduce the amount of trauma to the cells or cellular components which results from centrifugation.

Cell separation in the reagent-modified colloidal silica is accomplished by movement of the cells or cellular components during centrifugation to their buoyant densities within the density gradient. The cell bands which form at the respective buoyant densities can then be individually transferred to centrifuge tubes by pipette or preferably by cell removal tube. The processes of manufacture and use of said cell removal tube are described in my copending U.S. application Ser. No. 849,698 filed concurrently herewith, the disclosure of which is hereby incorporated by reference. The cell separation reagent can be removed by washing. The cells can then be pelleted and resuspended in buffer or growth medium.

This invention will be further understood from a consideration of the following Examples. It should be understood, however, that these Examples are given by way of illustration and not by way of limitation and that many changes or alterations may be made in, for example, quantities or choice of material without departing from the scope of this invention as recited in the claims.

EXAMPLE 1

Preparation of Reagent-Modified Colloidal Silica

Three liters of about 70 Å colloidal silica (50% by weight of silica) (purchased from Nyacol Products, Inc. Worchester, Mass.) was heated to 75° C. Two hundred and ten mls of gamma-glycidoxypropyltrimethoxysilane (purchased from Petrarch Systems, Inc.) was added at 2.0 mls per minute with continuous agitation. The reaction mixture was heated at 75° C., with agitation, for an additional 60 minutes following the last addition of reagent. The reaction mixture was then passed through an activated carbon column (8 cm diameter, 40 cm height) to remove any reaction by-products. The reagent-modified colloidal silica was then deionized by passing it through first a cation exchange resin column (hydrogen form) (8 cm ×40 cm) and then an anion exchange resin column (hydroxide form) (8 cm×40 cm) at 3.8 liters per hour. Three liters of water were then passed through the carbon and ion exchange resins to remove any remaining reagent-modified colloidal silica.

To facilitate the formation of additional covalent attachments between the reagent and the silica surface, the reagent-modified colloidal silica was then heated to 95° C. with vigorous agitation for 3 hours. Eight to 9 g/l solid sodium chloride and 0.3 to 0.4 g/l potassium chloride and 20 mM HEPES buffer in the hydrogen (2.51 g/l) and sodium (2.47 g/l) forms were then added to the reagent-modified colloidal silica preparation to adjust the osmotic pressure and pH respectively to physiological levels. The resulting solution was then diluted to a final density of 1.074–1.099 g/cm$^3$ by mixing with a HEPES buffered solution with identical osmotic pressure and pH. (See Table 4 in which the properties of two of the diluted reagent-modified colloidal silica compositions prepared as above are compared with two commercially available cell separation reagents, Percoll (registered trademark of Pharmacia) and Ludox HS-30 (registered trademark of DuPont)).

TABLE 4

Properties of Selected Colloid Silica Preparations

| | Colloidal Solutions | | | |
|---|---|---|---|---|
| | | | Reagent-Modified Colloidal Silica | |
| Property | Percoll[1] | Ludox HS-30[2] | Example 2 | Example 3 |
| Silica Content (%, w/w) | 20.0 | 30 | 10.6 | 13.7 |
| pH @ 20° C. | 8.9 ± 0.3 | 9.8 | 7.40 | 7.40–7.50 |
| Osmolality (mOsM/kg) | 20 | 36 | 300 | 300–320 |
| Density (g/cm$^3$) | 1.130 | 1.21 | 1.074 | 1.089–1.099 |
| Particle Size, Å | 150–300 | 130–140 | 70[3] | 220[3] |

[1]Percoll: Methodology and applications Pharmacia, Inc. 1982.
[2]J. Colloid and Interface Science 55: 25, 27 (1976).
[3]The particle size of the starting material according to manufacturer's specifications.

EXAMPLE 2

Separation of Mononuclear Cells From Blood

Three ml of diluted reagent-modified colloidal silica made from colloidal silica having a particle diameter of about 70 Å and having a density after dilution of about 1.074 g/cm$^3$ were placed in a 15 ml conical centrifuge tube. Three ml of blood diluted 1:1 with phosphate buffered saline (sodium chloride, 8 g/l; potassium chloride, 0.2 g/l; disodium hydrogen phosphate, 1.15 g/l; potassium dihydrogen phosphate, 0.2 g/l, pH 7.4) were layered onto the reagent-modified colloidal silica. The tube was centrifuged at 900×g for 20 minutes at room temperature in a swinging bucket rotor. The mononuclear cell band which collected at the meniscus was removed with a cell removal tube or a pipette. The mononuclear cells were washed by adding 10 ml of Hanks balanced salt solution, (potassium chloride, 0.4 g/l; potassium dihydrogen phosphate, 60 mg/l; sodium chloride, 8.0 g/l; sodium bicarbonate, 0.35 g/l; disodium hydrogen phosphate, 48 mg/l; glucose, 1 g/l; phenol red 10 mg/l, pH 7.4) and centrifuging at 300×g for 10 minutes at room temperature. The average percent recovery of lymphocytes was 62.3; the average viability of the cells was greater than 95%; the average percentage of lymphocytes was 77.6%. (See Table 4 for a comparison with recoveries obtained with selected commercially available cell separation reagents.)

EXAMPLE 3

Aseptic Separation of Mononuclear Cells From a Large Volume of Anti-Coagulated Whole Blood Four to 15 mls of EDTA anti-coagulated whole blood were added aseptically to a tube containing 6.7 mls of a filter sterilized diluted reagent-modified colloidal silica having a buoyant density after dilution of about 1.089 to about 1.099 g/cm$^3$. The blood and colloidal silica were mixed gently by inversion of the tube several times. The mononuclear cells were separated by centrifuging at 2000×g for 10 minutes at room temperature in a fixed angle rotor. The mononuclear cell band which formed just below the meniscus was removed aseptically with a sterile cell removal tube. The recovered cells were washed by adding 10 mls of sterile Hanks balanced salt solution and inverting the tube. The tube was then centrifuged at 300×g for 10 minutes at room temperature. For maximum lymphocyte recovery, 0.1% BSA was included in the wash buffer. The average recovery of lymphocytes was 84.8%; the average viability was 98.0% and the average purity of the lymphocyte population was 76.4%. (See Table 5 for a comparison of recoveries obtained with selected commercially available cell separation reagents. Also see Table 6 for an analysis of the percentage of blood component cell types recovered with the product used in this Example.)

TABLE 5

COMPARISON OF LYMPHOCYTE STIMULATION

| Seperation Medium | Recovery of Lymphocytes (%) | Viability of Lymphocytes (%) | Purity of Lymphocytes (%) | BLASTOGENESIS | | | | |
|---|---|---|---|---|---|---|---|---|
| | | | | Phytohemagglutinin | | | Pokeweed | |
| | | | | Unstim. (CPM) | Stim. (CPM) | Stim. Index | Stim. (CPM) | Stim. Index |
| Lympho-Paque | 53.9 | 96.6 | 79.6 | 634.2 | 153,791 | 392.2 | 10,336 | 25.1 |
| Example 2 | 62.3 | 97.8 | 77.6 | 632.2 | 138,214 | 266.9 | 17,189 | 37.3 |
| Ficoll-Paque | 56.3 | 96.3 | 80.0 | 627.2 | 112,102 | 207.9 | 11,902 | 26.7 |
| Percoll | 64.7 | 97.3 | 74.0 | 451.5 | 129,472 | 412.4 | 15,495 | 53.8 |
| Histo-Paque | 53.2 | 96.5 | 75.4 | 437.6 | 124,418 | 346.6 | 11,894 | 34.5 |
| Example 3 | 60.1 | 96.1 | 77.4 | 506.5 | 170,079 | 420.9 | 12,299 | 29.9 |

TABLE 6

Separation of Blood Into Component Cell Types

| Cell Type | % Total Cells |
| --- | --- |
| erythrocytes | 9.2* |
| lymphocytes | 76.4** |
| monocytes | 18.8** |
| basophils | 3.2** |
| neutrophils | 0.3** |
| eosinophils | 0** |
| immature | 1.1** |

*Expressed as a percentage of both white cells and red cells (erythrocytes) i.e. total cells.
Average Lymphocyte
Recovery 84.8
Average Viability 98.0
**Expressed as a percentage of only white cells excluding red cells (erythrocytes)

EXAMPLE 4

Separation of Mononuclear Cells From a Small Volume of Anti-Coagulated whole Blood One to 3 mls of EDTA anti-coagulated whole blood were added to a tube containing 6.7 mls of diluted reagent-modified colloidal silica having a density after dilution of about 1.089 to about 1.099 g/cm$^3$. One ml Hanks buffered salt solution, pH 7.4, was added. The blood and colloidal silica were mixed gently by inversion of the tube several times. The mononuclear cells were separated by centrifuging at 2000×g for 10 minutes at room temperature in a fixed angle rotor. The mononuclear cell band which formed just below the meniscus was removed with a cell removal tube. The recovered cells were washed by adding 10 mls of Hanks balanced salt solution and inverting the tube. The tube was then centrifuged at 300×g for 10 minutes at room temperature. For maximum lymphocyte recovery, 0.1% BSA was included in the wash buffer.

EXAMPLE 5

Aseptic Separation of Lymphocytes From a Large Volume of Anti-Coagulated Whole Blood Four to 15 mls of EDTA anti-coagulated whole blood were added aseptically to a tube containing 6.7 mls of filter-sterilized diluted reagent-modified collidal silica having a density after dilution of about 1.079 to about 1.089 g/cm$^3$. The blood and diluted reagent-modified colloidal silica were mixed gently by inversion of the tube several times. The mononuclear cells were separated by centrifuging at 2000×g for 15 minutes at room temperature in a fixed angle rotor. The monocyte and platelet cell band which formed just below the meniscus was removed with a sterile pipette and a sterile cell removal tube. The lymphocyte band which formed below the previous band was removed with the cell removal tube. The recovered cell bands were each washed by adding 10 mls of sterile Hanks balanced salt solution and inverting the tube. The tube was then centrifuged at 300×g for 10 minutes at room temperature. For maximum lymphocyte recovery, 0.1% BSA was included in the wash buffer.

EXAMPLE 6

Separation of Lymphocytes From a Small Volume of Anti-Coagulated Whole Blood

One to 3 mls of EDTA anti-coagulated whole blood were added to a tube containing 6.7 mls of a diluted reagent-modified colloidal silica having a buoyant density after dilution of about 1.079 to about 1.089 g/cm$^3$. The blood and diluted reagent-modified colloidal silica were mixed gently by inversion of the tube several times. The mononuclear cells were separated by centrifuging at 2000×g for 15 minutes at room temperature in a fixed angle rotor. The cell band comprising monocytes and platelets which formed just below the meniscus was removed with a pipette and cell removal tube. The lymphocyte band which formed below the previous band was removed with the cell removal tube. The recovered bands of cells were each washed by adding 10 mls of Hanks balanced salt solution and inverting the tube. The tube was then centrifuged at 300×g for 10 minutes at room temperature. For maximum lymphocyte recovery, 0.1% BSA was included in the wash buffer.

EXAMPLE 7

Separation of B and T Lymphocytes Cells From Whole Blood Using Clinical Research Kit A total of 6.7 mls of diluted reagent-modified colloidal silica which comprises 1.7 mls of reagent-modified colloidal silica made from about 70 Å colloidal silica, 4.0 mls of reagent-modified colloidal silica made from about 130-200 Å colloidal silica and 1.0 mls of reagent-modified colloidal silica made from about 600 Å colloidal silica is admixed with 1 to 5.0 mls of whole blood and centrifuged at 2000×g for 15 minutes in a fixed angle rotor. B lymphocytes form a band at a sharp break in the gradient. The B lymphocytes form a band separately above the T cell band. The B cell band is removed with a pipette and a cell removal tube. The T cell band is then removed using the cell removal tube. The collected cell bands are each washed with 10 ml of Hanks balanced salt solution, pH 7.4 and recovered by centrifuging at 300×g for 10 minutes at room temperature.

EXAMPLE 8

Separation of B-Lymphocytes Prior To Fusion With Myeloma Cells

One to six mls of a mouse spleen cell suspension, $1 \times 10^7$ to $5 \times 10^7$ cells/ml in Hanks balanced salt solution, pH 7.4, is mixed with 6.7 mls diluted reagent-modified colloidal silica and centrifuged at 2,000×g for 10 to 15 minutes in a fixed angle rotor. B lymphocytes are less dense than most of the other cells in the spleen and will form a band a few millimeters below the meniscus. The band of cells is collected using a cell removal tube. The cells are washed by adding 10 ml of Hanks balanced salt solution, pH 7.4, and centrifuging at 300×g for 10 minutes at room temperature. The separated cells can then be used directly for fusion with myeloma cells.

EXAMPLE 9

Separation of Cells Using Silica Particles Modified With Monoclonal Antibodies

One hundred mls partially reagent-modified colloidal silica particles (made from colloidal silica particles of about 600 Å) are reacted under aqueous conditions with 0.5 to 1.0 mls 3-mercaptopropyltrimethoxy silane to form thiol-modified colloidal silica which now contains thiol groups on the reagent-modified colloidal silica surface. The thiol-modified colloidal silica is reacted under aqueous conditions with 0.25 to 1.50 gms N-succinimidyl, 3-2-pyridyldithio proprionate (SPDP) which reacts with the thiols to form SPDP-modified colloidal silica. Twenty to 2,000 mgs Protein A is then added to the SPDP-modified colloidal silica. The SPDP forms an amide bond with the Protein A, thus coupling it to the particles to form Protein A-modified colloidal silica. Five to 200 ug monoclonal antibody (Mab) is then mixed with 0.1–1.0 mls Protein A-modified colloidal silica. The Protein A binds the Mab to form antibody-modified colloidal silica. The antibody-modified colloidal silica is admixed with 1 to 5.0 mls whole blood and incubated for 15 mins to allow the antibody to bind to antigen on the cells. The admixture is then separated by density gradient centrifugation on diluted reagent-modified colloidal silica. The cells to which antibody-modified colloidal silica is bound are altered in density and thus are easily separated. The antibody-modified colloidal silica with the cells bound is collected using a cell removal tube. The cells are removed from the antibody-modified colloidal silica by treatment with dithiothreitol or other sulfhydryl reducing agents such as glutathione or Beta-mercaptoethanol. The cells are then washed with 10 mls Hanks balanced salt solution, pH 7.4 and collected by centrifuging at 300×g for 10 minutes.

EXAMPLE 10

Separation of Cells Using Silica Particles Modified With Monoclonal Antibodies Fully reagent-modified colloidal silica is prepared using expoxyorganosilane or any of the organosilanes listed in Table 3. One hundred mls of fully reagent-modified colloidal silica (made from colloidal silica particles of about 600 Å) is reacted with 0.5 to 5.0 gms 1,1-carbonyldiimidazole or 0.3 to 3.0 gms succinimide under aqueous conditions to form carbodiimide-modified colloidal silica. The carbondiimide-modified colloidal silica is then reacted directly with 13 to 1,300 mgs Protein A in water to form Protein A-modified colloidal silica. Purified monoclonal antibody (Mab), 5 ug to 200 ug, is then mixed with 0.1 to 1.0 mls Protein A-modified colloidal silica. The Protein A binds the Mab to form antibody-modified colloidal silica. The antibody-modified colloidal silica is admixed with 1 to 6.0 mls whole blood and incubated for 15 mins. to allow the antibody-modified colloidal silica to bind to antigen on the cells. The admixture is then separated by density gradient centrifugation through diluted reagent-modified colloidal silica. The cells to which antibody-modified colloidal silica is bound are altered in density and thus are easily separated. The antibody-modified colloidal silica with the cells bound are collected using a cell removal tube. The cells are removed from the antibody-modified colloidal silica by treatment with ethanolamine. The cells are then washed with 10 mls Hanks balanced salt solution, pH 7.4 and collected by centrifuging at 300×g for 10 minutes.

EXAMPLE 11

Separation of Human X and Y Bearing Sperm Cells From Semen Specimen

One to six mls of a semen sample containing $1 \times 10^7$ to $2 \times 10^7$ sperm/ml is admixed with 6.7 mls diluted reagent-modified colloidal silica which has a density after dilution of 1.185 g/cm$^3$, a density which is intermediate between the densities of X and Y sperm. The gradient material consists of 1.7 mls of reagent-modified colloidal silica made from colloidal silica of about 70 Å and 5.0 mls of reagent-modified colloidal silica made from colloidal silica of about 200 Å. The admixture is centrifuged at 2,000×g for 10 to 15 minutes in a fixed angle rotor. The density of Y sperm is less than X sperm due to the lower DNA content per sperm. The Y sperm are removed using a pipette and cell removal tube. The X sperm are removed using a cell removal tube. The separation is monitored by fluorescence staining of the separated spermatozoa using acridine orange and quantitated by use of a Fluorescence Activited Cell Sorter (FACS) laser system. The greater DNA content of the X sperm produces a greater fluorescent image relative to the Y sperm. *Biol. Reprod.* 28: 312–321 (1983).

EXAMPLE 12

Formation of Gradient Shapes Using A Combination of Particle Sizes

A total of 6.0 mls of an admixture of distinct populations of diluted reagent-modified colloidal silica, each having a density of 1.089 g/cm$^3$ after dilution, was mixed with 3.0 mls whole blood and centrifuged for 10 minutes in a fixed angle rotor at 2,000×g at room temperature. Distinct populations of reagent-modified colloidal silica were admixed as indicated in Table 7.

TABLE 7

Admixtures of Distinct Populations of Reagent-Modified Colloidal Silica

| Curve in FIG. 1 | about 70 Å | Colloidal Silica Particle Size about 130 Å to about 200 Å | about 600 Å |
|---|---|---|---|
| A | 2.0 mls | 1.0 ml | 3.0 mls |
| B | 2.0 mls | 2.0 mls | 2.0 mls |
| C | 1.0 ml | 4.0 mls | 1.0 ml |
| D | 2.0 mls | 3.0 mls | 1.0 ml |
| E | 1.0 ml | 3.0 mls | 2.0 mls |
| F | 1.0 ml | 2.0 mls | 3.0 mls |
| G | 0 | 6.0 mls | 0 |
| H | 0 | 5.0 mls | 1.0 ml |
| I | 0 | 4.0 mls | 2.0 mls |

Density marker beads (Pharmacia) were used to measure the density at which cells in the blood sample formed bands. The results for the combinations listed in Table 7 are shown in FIG. 1.

I claim:

1. A cell separation composition comprising a stable aqueous colloidal suspension of reagent-modified colloidal silica particles, which suspension is comprised of a plurality of colloidal silica particles, each particle covalently linked to an organosilane having a non-ionic, hydrophilic group.

2. The composition of claim 1 wherein said organosilane is of the general formula:

$(X)_3-Si-(CH_2)_3-Y$ and wherein "Y" is selected from the group consisting of

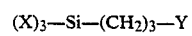

$OCH_2CHCH_2O$, $O_2CCH_3$, $N(CH_2CH_2OH)_2$, $CO_2CH_3$, $NH(CH_2)_2NH(CH_2)_2CO_2CH_3$, $NHCOCH_2NHC(CH_3)O$,

$N-CH_2-CH_2-O-CH_2CH_2$, and

-continued

and wherein "X" is selected from the group consisting of $H_3CO$, $Cl$, $H_5C_2O$, $H_3CCO_2$, and $H_3C$.

3. The composition of claim 1 wherein said organosilane is of the general formula:

$(X)_3$—Si—$(CH_2)_2$—Y and wherein "Y" is selected from the group consisting of

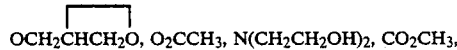

$NH(CH_2)_2NH(CH_2)_2CO_2CH_3$, $NHCOCH_2NHC(CH_3)O$,

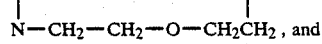

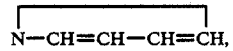

and wherein "X" is selected from the group consisting of $H_3CO$, $Cl$, $H_5C_2O$, $H_3CCO_2$, and $H_3C$.

4. The composition of claim 1 wherein said organosilane comprises gamma-glycidoxypropyltrimethoxysilane.

5. The composition of claim 1 wherein each of said colloidal silica particles are between about 30 Å to about 600 Å in diameter before modification.

6. The composition of claim 1 wherein said reagent-modified colloidal silica particles are suspended in a buffer.

7. The composition of claim 1 wherein each of said colloidal silica particles is of about the same diameter.

8. The composition of claim 1, wherein said reagent-modified colloidal silica particles have a buoyant density between about 1.06 $g/cm^3$ and about 1.43 $g/cm^3$.

9. The composition of claim 1, wherein said suspension comprises a first distinct population of said reagent-modified colloidal silica particles admixed with a second distinct population of said reagent-modified colloidal silica particles, said first distinct population consisting of reagent-modified colloidal silica particles each of approximately a first diameter, and said second distinct population consisting of reagent-modified colloidal silica particles each of approximately a second diameter.

10. The composition of claim 1, wherein said suspension comprises a first distinct population of reagent-modified colloidal silica particles admixed with a second distinct population of reagent-modified colloidal silica particles and a third distinct population of reagent-modified colloidal silica particles, said first distinct population consisting of reagent-modified silica particles each of approximately a first diameter, said second distinct population consisting of reagent modified silica particles each of approximately a second diameter, and said third distinct population consisting of reagent-modified silica particles each of approximately a third diameter.

11. The composition of claim 1, wherein said composition is sterile.

* * * * *

UNITED STATES PATENT AND TRADEMARK OFFICE
CERTIFICATE OF CORRECTION

PATENT NO. : 4,927,749

DATED : May 22, 1990

INVENTOR(S) : Allan R. Dorn

Page 1 of 2

It is certified that error appears in the above-identified patent and that said Letters Patent is hereby corrected as shown below:

Page 1, under "Foreign Patent Documents," entry should be --WO8202403 07/1982 PCT Int'l Appln.--

Page 1, Abstract, add the following sentence at the end: --The cell separation composition contains colloidal silica particles covalently linked to an organosilane having a non-ionic, hydrophilic group.--

Column 4, line 53, "$\geq$" should be --$\geq$--.

Column 6, line 47, "$\geq$" should be --$\geq$--.

Column 7, line 16, "d and" should be --and d--.

Column 8, line 9, "(g/m$^3$)" should be --(g/cm$^3$)--.

Column 9, line 16, delete "H$^3$CO".

Column 9, line 19, after "($\gamma$-glycidoxypropyl)trimethoxy-silane" insert [under column heading "Where X ="] --H$^3$CO--.

UNITED STATES PATENT AND TRADEMARK OFFICE
CERTIFICATE OF CORRECTION

PATENT NO. : 4,927,749
DATED : May 22, 1990
INVENTOR(S) : Allan R. Dorn

It is certified that error appears in the above-identified patent and that said Letters Patent is hereby corrected as shown below:

Column 12, line 26, after "÷" delete "X".

Column 13, line 17, after "acid" insert --(TAPSO), [N-TRIS(hydroxymethyl)methyl-2-amino]Ethanesulfonic acid--.

Column 20, line 38 [last entry in Table 7]

"I        0  4.0        mls 2.0        mls"

should be

--I        0        4.0 mls        2.0 mls--

Signed and Sealed this

Twenty-eighth Day of December, 1993

Attest:

BRUCE LEHMAN

Attesting Officer      Commissioner of Patents and Trademarks